United States Patent [19]
Kover et al.

[11] Patent Number: 6,084,098
[45] Date of Patent: Jul. 4, 2000

[54] BENZYLPIPERAZINYL AND PIPERIDINYL ETHANONE DERIVATIVES: DOPAMINE RECEPTOR SUBTYPE SPECIFIC LIGANDS

[75] Inventors: Renata Xavier Kover, New Haven; Silva Terdjanian, New Britain; Jennifer Tran, Branford; Andrew Thurkauf, Danbury, all of Conn.

[73] Assignee: Neurogen Corporation, Branford, Conn.

[21] Appl. No.: 09/259,239

[22] Filed: Feb. 26, 1999

Related U.S. Application Data

[60] Provisional application No. 60/076,043, Feb. 26, 1998.

[51] Int. Cl.$^7$ .................. C07D 403/06; C07D 401/06
[52] U.S. Cl. ............... 544/373; 544/363; 544/359; 544/358; 544/400; 544/60; 544/105; 540/66; 540/468; 540/476
[58] Field of Search ..................... 544/358, 359, 544/363, 373, 400, 60, 105, 70, 8; 540/66, 468, 476

[56] References Cited

PUBLICATIONS

Ohtaka, H. et al.: benzylpiperazine derivatives. IX. Structure–antiulcer activity studies of 1-(Aminocarbonylalkyl)-4-benzylpiperazine derivatives by the adaptive least-squares method. Chem. Pharm. Bull. vol. 36, pp. 3955–3960, 1988.

*Primary Examiner*—Charanjit S. Aulakh
*Attorney, Agent, or Firm*—McDonnel Boehnen Hulbert & Berghoff; Steven J. Sarussi

[57] ABSTRACT

Disclosed are compounds of the formula:

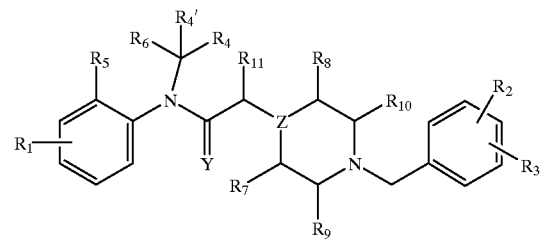

or pharmaceutically acceptable addition salts thereof wherein:

Y represents oxygen or sulfur; Z is nitrogen or CH;

$R_1$, $R_2$ and $R_3$ independently represent organic or inorganic substituents;

$R_4$ and $R_4'$ independently represent hydrogen, alkyl or form a ring with the atom to which they are attached;

$R_5$ represents hydrogen, alkyl, alkoxy, or alkylthio, and $R_6$ represents hydrogen or alkyl; or $R_5$ and $R_6$ form a ring together with the atoms to which they are attached; and $R_7$, $R_8$, $R_9$, $R_{10}$ and $R_{11}$ independently represent hydrogen or alkyl, which compounds are useful for the treatment and/or prevention of neuropsychological disorders including, but not limited to, schizophrenia, mania, dementia, depression, anxiety, compulsive behavior, substance abuse, Parkinson-like motor disorders and motion disorders related to the use of neuroleptic agents.

32 Claims, No Drawings

BENZYLPIPERAZINYL AND PIPERIDINYL ETHANONE DERIVATIVES: DOPAMINE RECEPTOR SUBTYPE SPECIFIC LIGANDS

CROSS-REFERENCE

This application claims benefit of Provisional application No. 60/076,043, filed Feb. 26, 1998.

BACKGROUND OF THE INVENTION

1. Field of the Invention

This invention relates to substituted 2-(4-benzylpiperazin-1-yl) and 2-(1-benzylpiperidin-4-yl)ethanones and to pharmaceutical compositions containing such compounds. It also relates to the use of such compounds in the treatment or prevention of psychotic disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has been identified (Nature, 347: 146 (Sokoloff et al., 1990)). Its unique localization in limbic brain areas and its differential recognition of various antipsychotics suggest that the $D_4$ receptor may play a major role in the etiology of schizophrenia. Selective $D_4$ antagonists are considered effective antipsychotics free from the neurological side effects displayed by conventional neuroleptics.

Various 4-benzylpiperazines have been described. See, for example, Arch. Med. Res., 25: 435–440 (Terron et al., 1994) and Toxicol. Appl. Pharmacol., 7: 257–267 (Schmidt and Martin, 1965).

SUMMARY OF THE INVENTION

The invention provides novel compounds which interact with dopamine receptor subtypes. Accordingly, in a broad aspect, the invention provides compounds of Formula I:

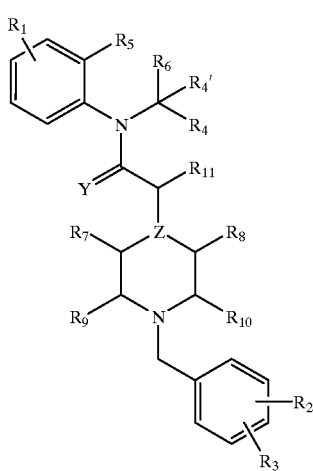

I wherein:
Y represents oxygen or sulfur;
Z is nitrogen or CH;
$R_1$, $R_2$ and $R_3$ independently represent hydrogen, halogen, hydroxy, lower alkoxy, $C_1$–$C_6$ alkyl, trifluoromethyl or trifluoromethoxy;

$R_4$ and $R_4'$ independently represent hydrogen or $C_1$–$C_6$ alkyl; or $R_4$ and $R_4'$ together with the atom to which they are attached form a ring having from 3–7 members;

$R_5$ represents hydrogen, $C_1$–$C_6$ alkyl, $C_1$–$C_6$ alkoxy, or $C_1$–$C_6$ alkylthio;

$R_6$ is hydrogen or $C_1$–$C_6$ alkyl; or $R_5$ and $R_6$ together represent $C_1$–$C_5$ alkylene, $C_1$–$C_4$ alkyleneoxy, $C_1$–$C_4$ alkylenethio where the oxygen or sulfur atoms are immediately adjacent the phenyl ring, and together with the atoms to which they are attached form a ring having from 5–9 members; and $R_7$, $R_8$, $R_9$, $R_{10}$, and $R_{11}$ independently represent hydrogen or $C_1$–$C_6$ alkyl.

Dopamine $D_4$ receptors are concentrated in the limbic system (Science, 265: 1034 (Taubes, 1994)) which controls cognition and emotion. Therefore, compounds that interact with these receptors are useful in the treatment of cognitive disorders. Such disorders include cognitive deficits which are a significant component of the negative symptoms (social withdrawal and unresponsiveness) of schizophrenia. Other disorders include those involving memory impairment or attention deficit disorders.

Compounds of the present invention demonstrate high affinity and selectivity in binding to the $D_4$ receptor subtype. These compounds are therefore useful in treatment of a variety of neuropsychological disorders, such as, for example, schizophrenia, psychotic depression and mania. Other dopamine-mediated diseases such as Parkinsonism and tardive dyskinesias can also be treated directly or indirectly by modulation of $D_4$ receptors.

Compounds of this invention are also useful in the treatment of depression, memory-impairment or Alzheimer's disease by modulation of $D_4$ receptors since they exist selectively in areas known to control emotion and cognitive functions.

Thus, in another aspect, the invention provides methods for treatment and/or prevention of neuropsychochological or affective disorders including, for example, schizophrenia, mania, dementia, depression, anxiety, compulsive behavior, substance abuse, memory impairment, cognitive deficits, Parkinson-like motor disorders, e.g., Parkinsonism and dystonia, and motion disorders related to the use of neuroleptic agents. In addition, the compounds of the invention are useful in treatment of depression, memory-impairment or Alzheimer's disease. Further, the compounds of the present invention are useful for the treatment of other disorders that respond to dopaminergic blockade, e.g., substance abuse and obsessive compulsive disorder. These compounds are also useful in treating the extrapyramidal side effects associated with the use of conventional neuroleptic agents.

In yet another aspect, the invention provides pharmaceutical compositions comprising compounds of Formula I.

In a yet further aspect, the invention provides intermediates useful for preparing compounds of Formula I.

DETAILED DESCRIPTION OF THE INVENTION

As mentioned above, the invention encompasses substituted 2-(4-benzyl)-piperazinyl- and piperidinyl-1-ethanones of Formula I. Preferred compounds of Formula I are those where $R_2$ and $R_3$ are not both hydrogen simultaneously. Other preferred compounds of Formula I are those where $R_7$, $R_8$, $R_9$, and $R_{10}$ are hydrogen. In the compounds of the invention, $R_{11}$ is preferably hydrogen, methyl or ethyl, most preferably hydrogen.

As noted, the invention encompasses compounds where $R_5$ and $R_6$ together represent $C_1$–$C_5$ alkylene, $C_1$–$C_4$ alkyleneoxy, and $C_1$–$C_4$ alkylenethio. In these compounds, the oxygen or sulfur atoms are immediately adjacent the phenyl ring carrying the $R_5$ group. In such cases, $R_5$ and $R_6$ together with the atoms to which they are attached form a ring having from 5–9 members. Examples of such rings include the following:

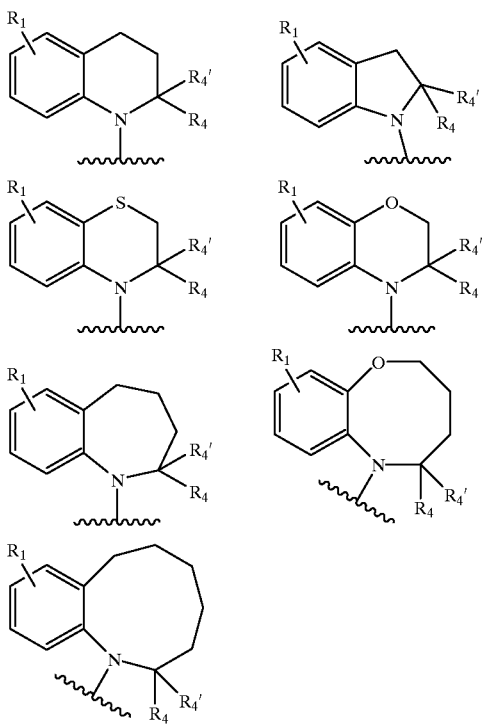

Preferred among these bicyclic ring systems are compounds where n is 0 or an integer of 1 or 2.

In these compounds, $R_4$ and $R_4'$ independently represent hydrogen or $C_1$–$C_6$ alkyl, or $R_4$ and $R_4'$ together with the atom to which they are attached form a ring having from 3–7 members. Representative resulting spiro ring systems include the following:

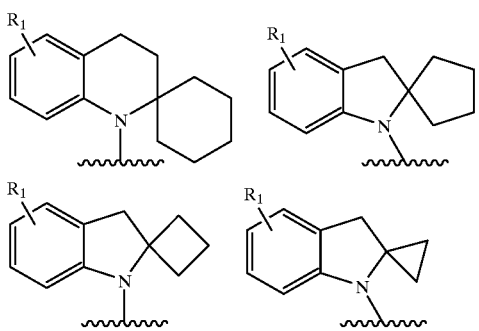

Compounds in which $R_5$ and $R_6$ together with the atoms to which they are attached form a ring having from 5–9 members as discussed above are represented by Formula II:

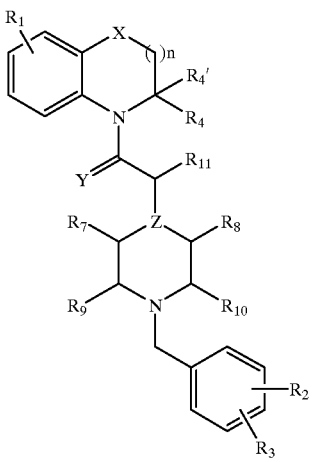

wherein X represents oxygen, or sulfur, or CH;

Y is oxygen or sulfur;

Z is nitrogen or CH;

n is zero or an integer of from 1–4;

$R_1$, $R_2$ and $R_3$ independently represent hydrogen, halogen, hydroxy, lower alkoxy, $C_1$–$C_6$ alkyl, trifluoromethyl or trifluoromethoxy;

$R_4$ and $R_4'$ independently represent hydrogen or $C_1$–$C_6$ alkyl; or $R_4$ and $R_4'$ together with the atom to which they are attached form a ring having from 3–7 members;

$R_7$, $R_8$, $R_9$, $R_{10}$, and $R_{11}$ independently represent hydrogen or $C_1$–$C_6$ alkyl.

Preferred compounds of Formula II are those where $R_2$ and $R_3$ are not simultaneously hydrogen. In preferred compounds of Formula II, $R_4$ and $R_4'$ are independently hydrogen or $C_1$–$C_4$ alkyl. In other preferred compounds of Formula II, n is 0 or 1, and more preferably 0.

A preferred group of compounds of Formula II are those where Y is oxygen, X is $CH_2$ and Z is CH. Such compounds are depicted by Formula IIa:

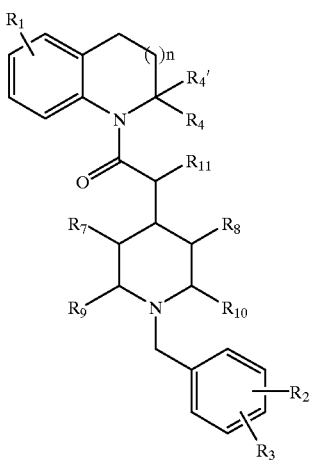

wherein n, $R_1$, $R_2$, $R_3$, $R_4$, $R_4'$ $R_7$, $R_8$, $R_9$, $R_{10}$, and $R_{11}$ are as defined above for Formula II.

In the compounds of Formula IIa, $R_{11}$ is preferably hydrogen, methyl or ethyl. In preferred compounds of Formula IIa, $R_1$ is hydrogen or halogen, and $R_2$ and $R_3$ are independently selected from hydrogen, $C_1$–$C_6$ alkyl, and halogen. More preferred such compounds of Formula IIa are those where $R_{11}$ is hydrogen or methyl, $R_1$ is hydrogen or halogen, and not both of $R_2$ and $R_3$ are hydrogen simultaneously. Particularly preferred compounds of Formula IIa are those where $R_{11}$ is hydrogen or methyl, $R_2$ is hydrogen, $R_3$ is methyl, methoxy, chloro, or fluoro, $R_4$ and $R_4'$ are independently hydrogen or lower alkyl, most preferably $C_1$–$C_2$ alkyl, and $R_1$ is hydrogen or halogen.

Another preferred group of compounds of Formula II are those where Z is nitrogen and X is $CH_2$. Such compounds are generally represented by Formula IIb:

IIb

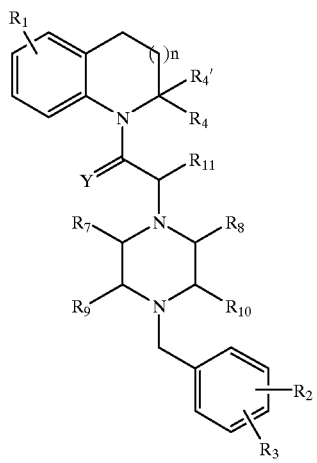

wherein n, Y, $R_1$, $R_2$, $R_3$, $R_4$, $R_4'$ $R_7$, $R_8$, $R_9$, $R_{10}$, and $R_{11}$ are as defined above for Formula II.

In such compounds, $R_{11}$ is preferably hydrogen, methyl or ethyl. Further, in such preferred compounds, Y is oxygen, $R_1$ is hydrogen or halogen, and $R_2$ and $R_3$ are independently selected from hydrogen, $C_1$–$C_6$ alkyl, and halogen. More preferred compounds of Formula IIb are those where $R_{11}$ is hydrogen or methyl, Y is oxygen, $R_1$ is hydrogen or halogen, and not both of $R_2$ and $R_3$ are hydrogen simultaneously. Particularly preferred compounds of Formula IIb where $R_{11}$ is hydrogen or methyl, Y is oxygen, $R_2$ is hydrogen, $R_3$ is methyl, methoxy, chloro, or fluoro, $R_4$ and $R_4'$ are independently hydrogen or lower alkyl, most preferably $C_1$–$C_2$ alkyl, and $R_1$ is hydrogen or halogen.

Compounds of Formula I where $R_5$ is hydrogen or lower alkyl and $R_6$ are is hydrogen are represented by Formula III:

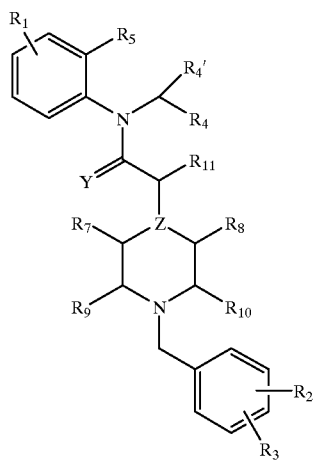

wherein Y, Z, $R_1$, $R_2$, $R_3$, $R_4$, $R_4'$ $R_5$, $R_7$, $R_8$, $R_9$, $R_{10}$, and $R_{11}$ are as defined above for Formula I. In the compounds of Formula III, $R_2$ and $R_3$ are preferably not both hydrogen simultaneously.

A preferred group of compounds of Formula III, hereinafter Formula IIIa, are those where Y is oxygen, Z is nitrogen, $R_1$ is hydrogen or halogen, and $R_2$ and $R_3$ are independently selected from hydrogen, $C_1$–$C_6$ alkyl, and halogen. Still more preferred compounds of Formula IIIa are those where not both of $R_2$ and $R_3$ are hydrogen simultaneously. Other preferred compounds of Formula IIIa are those where $R_2$ is hydrogen, $R_3$ is methyl, chloro, or fluoro, and one or both of $R_4$ and $R_4'$ are lower alkyl, most preferably $C_1$–$C_2$ alkyl, and $R_1$ is hydrogen or halogen. Particularly preferred compounds of Formula IIIa are those where $R_2$ is hydrogen and $R_3$ is a methyl, chloro, or fluoro group in the 4 position on the phenyl ring. Other particularly preferred compounds of Formula IIIa are those where the phenyl substituted with $R_2$ and $R_3$ is 2-alkoxy-5-halophenyl. Representative of such particularly preferred compounds are those where the phenyl carrying $R_2$ and $R_3$ is 2-($C_1$–$C_2$) alkoxy-5-fluoro or 5-chlorophenyl.

Another preferred group of compounds of Formula III, hereinafter Formula IIIb, are those where Y is oxygen, Z is CH, $R_1$ is hydrogen or halogen, and $R_2$ and $R_3$ are independently selected from hydrogen, $C_1$–$C_6$ alkyl, and halogen. Still more preferred compounds of Formula IIIb are those where not both of $R_2$ and $R_3$ are hydrogen simultaneously. Other preferred compounds of Formula IIIb are those where $R_2$ is hydrogen, $R_3$ is methyl, chloro, or fluoro, and one or both of $R_4$ and $R_4'$ are lower alkyl, most preferably $C_1$–$C_2$ alkyl, and $R_1$ is hydrogen or halogen. Particularly preferred compounds of Formula IIIb are those where $R_2$ is hydrogen and $R_3$ is a methyl, chloro, or fluoro group in the 4 position on the phenyl ring. Other particularly preferred compounds of Formula IIIb are those where the phenyl substituted with $R_2$ and $R_3$ is 2-alkoxy-5-halophenyl. Representative of such particularly preferred compounds are those where the phenyl carrying $R_2$ and $R_3$ is 2-($C_1$–$C_2$) alkoxy-5-fluoro or -5-chlorophenyl.

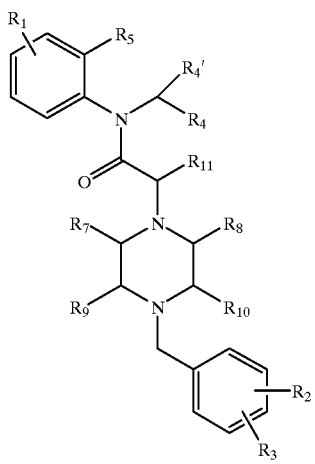

IIIa

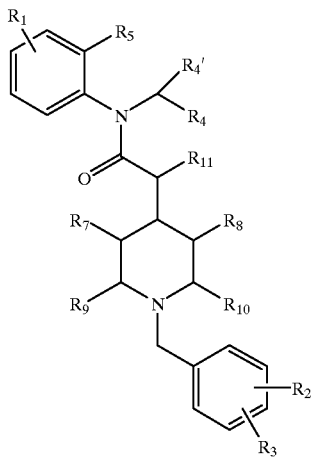

IIIb

The substituents on Formulae IIIa and IIIb are as defined above for Formula III.

Another preferred group of compounds of the invention is encompassed by Formula IV, i.e., where $R_5$ and $R_6$ together form a ring and $R_4$ and $R_4'$ also together form a ring:

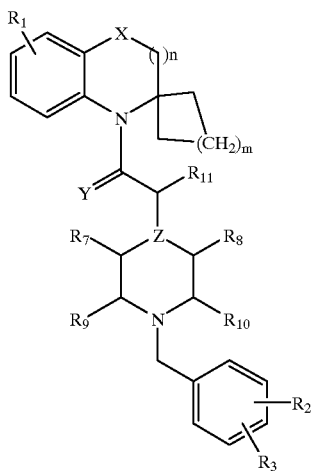

IV wherein X, n, Y, Z, $R_1$, $R_2$, $R_3$, $R_7$, $R_8$, $R_9$, $R_{10}$, and $R_{11}$ are as defined above for Formula I, and m is zero or an integer of from 1–4. Preferably, $R_2$ and $R_3$ are not both hydrogen simultaneously in the compounds of Formula IV.

Preferred compounds of Formula IV are those where X is $CH_2$, n is 0, $R_4$ and $R_4'$ form a five-membered carbocyclic ring with the atom to which they are attached (i.e., m is 2), and $R_{11}$ is hydrogen. Where Z in Formula IV is CH, the resulting compounds having m=2 are designated Formula IVa. Where Z in Formula IV is nitrogen, the resulting compounds having m=2 are designated Formula IVb.

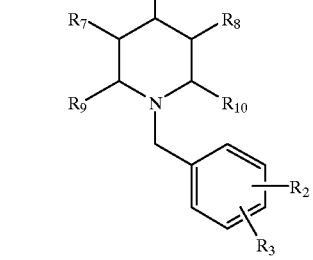

IVa

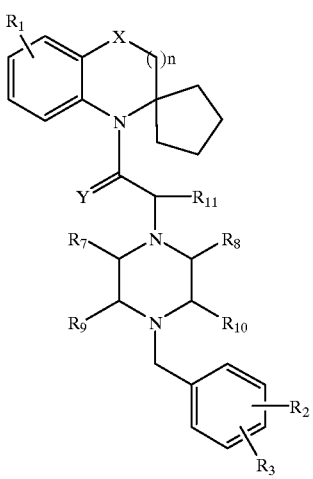

IVb

In preferred compounds of each of Formulae IVa and IVb, X is $CH_2$, Y is oxygen, and n is 0. More preferred compounds are those where X is $CH_2$, Y is oxygen, and n is 0, $R_1$ is hydrogen or halogen, and $R_2$ and $R_3$ are independently selected from hydrogen, $C_1$–$C_6$ alkyl, and halogen. Still more preferred compounds of these formulae are those where X is $CH_2$, Y is oxygen, and n is 0 and not both of $R_2$ and $R_3$ are hydrogen simultaneously. Other preferred compounds of Formulae IVa and IVb are those where Z is CH, Y is oxygen, $R_2$ is hydrogen, and $R_3$ is methyl, fluoro or chloro. Particularly preferred compounds of these formulae are those where X is $CH_2$, Y is oxygen, and n is 0, $R_2$ is hydrogen and $R_3$ is a methyl, chloro or fluoro group in the 4 position on the phenyl ring. Other particularly preferred compounds of these formulas are those where the phenyl substituted with $R_2$ and $R_3$ is 2-alkoxy-5-halophenyl.

Also encompassed within the scope of the invention are intermediates useful in preparing compounds of the invention. Thus, the invention provides compounds of Formula VII-a:

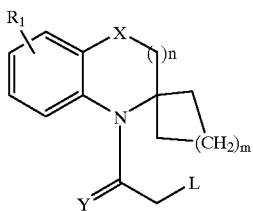

VII-a wherein X, n, Y, and $R_1$ are as defined above for Formula I, m is zero or an integer of from 1–4, and L is a leaving group, such as, for example, halogen, methane sulfonyl, or toluenesulfonyl. A preferred group of compounds of Formula VII-a are those where Y is oxygen, X is oxygen or, more preferably, methylene, m is 2, and $R_1$ is hydrogen or halogen.

Another group of intermediates is encompassed by Formula VII-b:

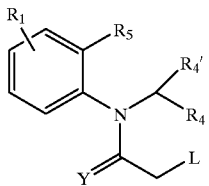

VII-b wherein Y, $R_1$ $R_4$, $R_4'$ $R_5$ are as defined above for Formula I, and L is a leaving group.

A preferred group of compounds of Formula VII-b are those where Y is oxygen or, more preferably, methylene, and $R_1$ is hydrogen or halogen. Other preferred compounds of Formula VII-b are those where one or both of $R_4$ and $R_4'$ are lower alkyl, most preferably $C_1$–$C_2$ alkyl, and $R_1$ is hydrogen or halogen.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n—ACOOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By "alkyl" or "lower alkyl" in the present invention is meant $C_1$–$C_6$ alkyl, i.e., straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkoxy" or "lower alkoxy" in the present invention is meant $C_1$–$C_6$ alkoxy, i.e., straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

Representative compounds of the invention are shown below in Table 1.

TABLE 1

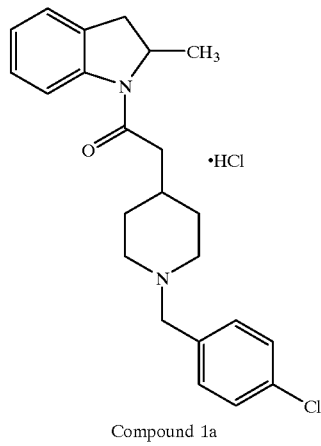

Compound 1a

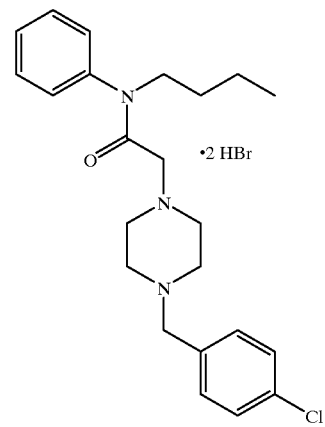

Compound 2a

TABLE 1-continued

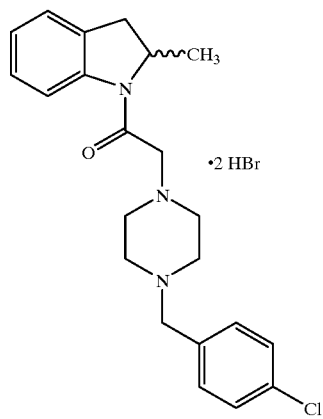

Compound 3a

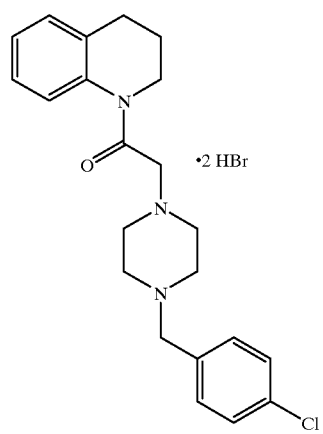

Compound 4a

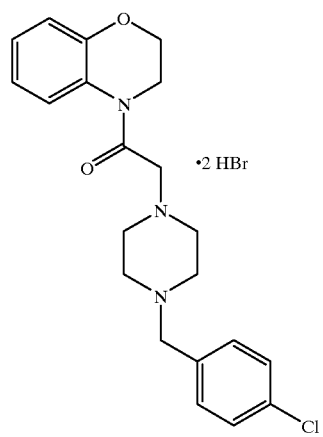

Compound 5a

TABLE 1-continued

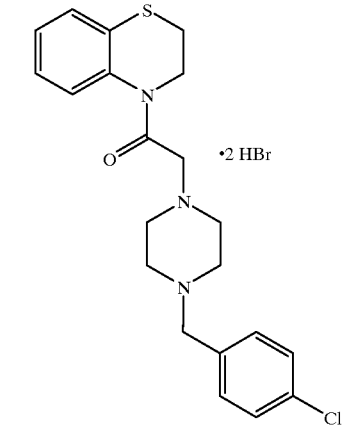

Compound 6a

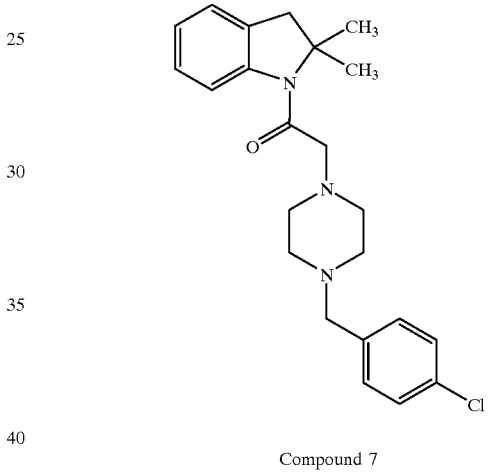

Compound 7

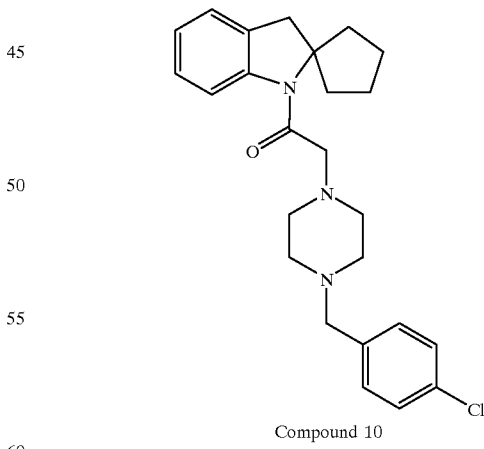

Compound 10

The compounds of the invention are useful in the treatment of neuropsychological disorders; the pharmaceutical utility of compounds of this invention is indicated by the assays for dopamine receptor subtype affinity described below in the Examples. The interaction of the substituted 2-(4-Phenylmethyl)-piperazino-1-ethanones of the invention with dopamine receptor subtypes results in the pharmacological activities of these compounds.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Representative illustrations of methods suitable for the preparation of compounds of the present invention are shown in the following Schemes. Those having skill in the art will recognize that the starting materials may be varied and additional steps employed to produce compounds encompassed by the present invention. For example, in certain situations, protection of reactive moieties such as amino groups, will be required.

A 2-(4-benzylpiperazin-1-yl-1-ethanone compound of Formula I may be prepared according to the reactions shown in Scheme 1.

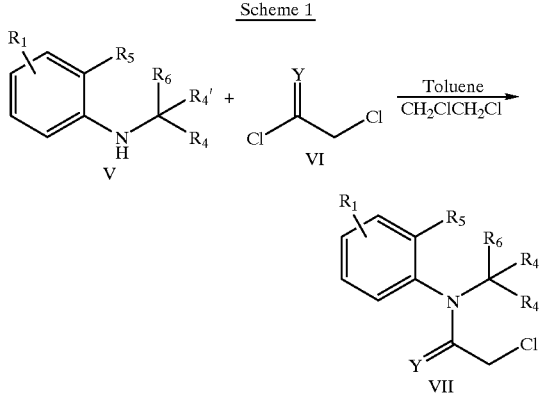

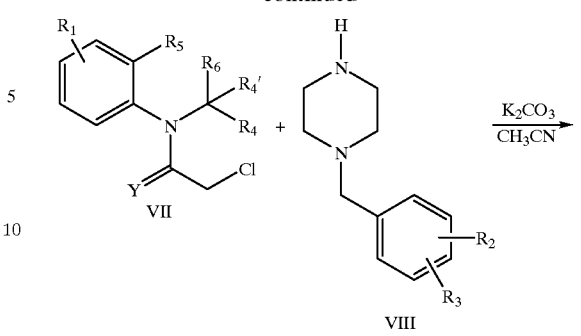

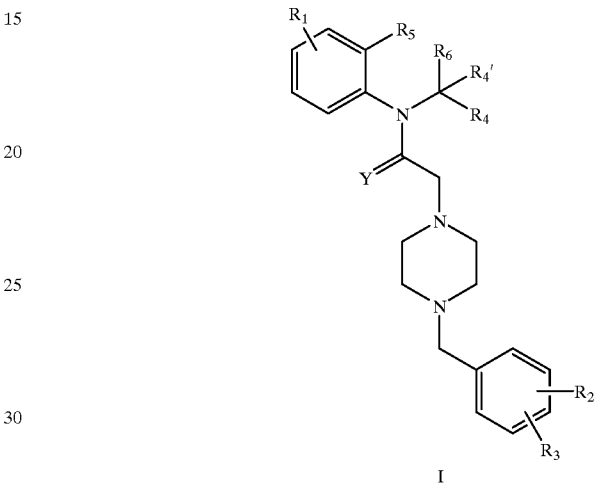

wherein $R_1$, $R_2$, $R_3$, $R_4$, $R_4'$, $R_5$, $R_6$, and Y are as defined above for Formula I.

As shown in Scheme 1, an aniline of general structure V having an appropriate secondary amino group is condensed with chloroacetyl chloride or an appropriate derivative thereof (VI). The resulting intermediate VII in turn is reacted with a piperazine derivative of general structure VII to provide a 2-(4-benzylpiperazin-1-yl)-1-ethanone derivative of Formula I. The piperazine derivatives VIII are generally commercially available but may also be prepared using methods described in the literature.

The 2-(4-benzylpiperazin-1-yl)-1-ethanones of the invention may be prepared according to the reactions shown below in Scheme 2.

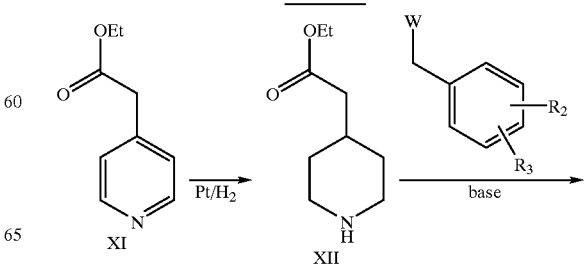

-continued

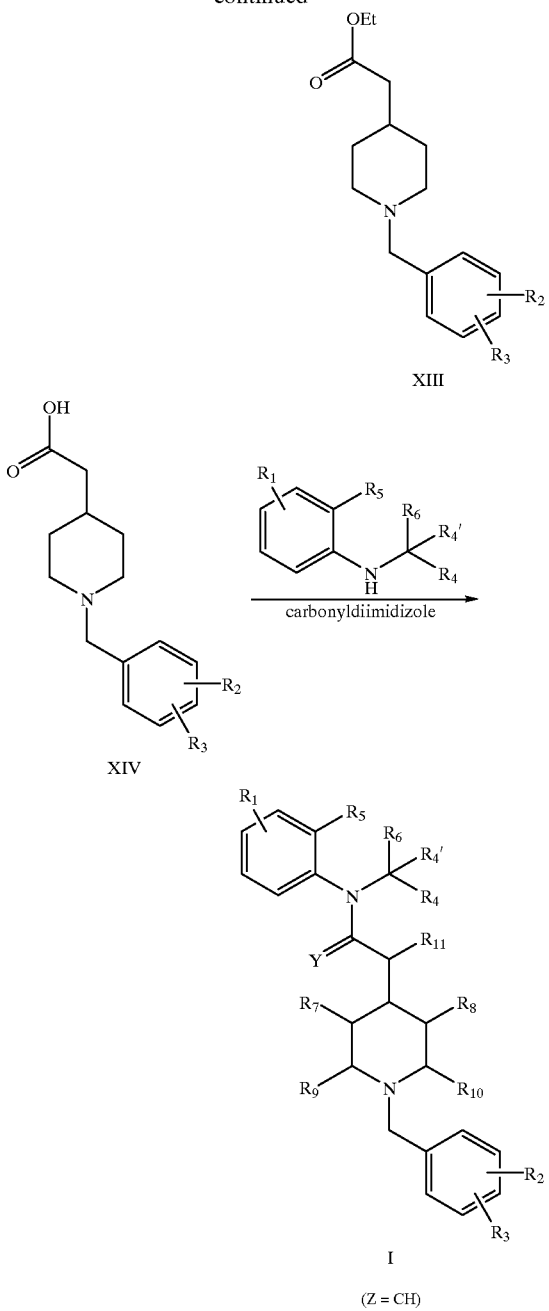

XIII

XIV

I (Z = CH)

wherein the substituents carry the same definitions as set forth above for Formula I.

As shown in Scheme 2, an ester of pyridine-4-acetic acid (XI) may be reduced with hydrogen gas in the presence of a catalyst, e.g., platinum, to provide piperidine aminoester derivative XII. Aminoester XII may be condensed with an appropriate benzylic alkylating agent containing a leaving group W, wherein W may be a halogen or a sulfonate ester or the like, to provide an N-benzylpiperidine of general structure XIII. The ester group of XIII may be saponified in base to provide an amino acid of general structure XIV which is subsequently condensed with a secondary amine to provide the desired compounds of Formula I wherein Z is a methine carbon (Z=CH).

Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, the need for such protecting groups will be apparent to those skilled in the art of organic synthesis as well as the conditions necessary to attach and remove such groups.

The invention is illustrated further by the following examples which are not to be construed as limiting the invention in scope or spirit to the specific procedures described in them.

EXAMPLE 1

Preparation of Starting Materials and Intermediates

The starting materials and various intermediates may be obtained from commercial sources, prepared from commercially available organic compounds, or prepared using well known synthetic methods.

A representative example of a method for preparing the ethanone intermediates of the invention is set forth below.

2-chloro-1-indolinylethan-1-one

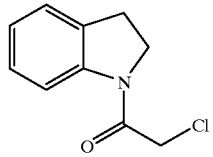

A quantity of 2,3-dihydro-1H-1-indole (also known as indoline, 2.1 g, 17.6 mmol) is dissolved in toluene (60 ml). To the solution of the amine in toluene is added acetyl chloride (2.0 g, 17.6 mmol) dissolved in 1,2-dichloroethane (20 ml). The reaction mixture turns brown upon addition of the acid chloride. The reaction is allowed to proceed at room temperature, with stirring, for about 3 hr, after which the reaction mixture is diluted with ethyl acetate and washed with 50:50 (v/v) water:saturated NaCl solution (2 times). The organic phase is dried over anhydrous MgSO$_4$ and concentrate to yield 2-Chloro-1-(2,3-dihydro-1H-1-indolyl)-1-ethanone (may also be named 2-chloro-1-indolinylethan-1-one) in 85% yield (2.92 g, 15 mmol) as a light brown solid.

EXAMPLE 2

2-(4-(4-chlorobenzyl)piperazinyl)-1-indolinylethan-1-one

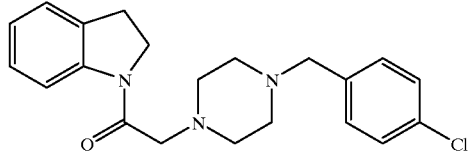

To a solution of (4-chlorobenzyl)-piperazine (1.5 g, 7.2 mmol) in acetonitrile (100 ml) is added 2-Chloro-1-(2,3-dihydro-1H-1-indolyl)-1-ethanone (1.4 g, 7.16 mmol) and K$_2$CO$_3$ (12 g, 87 mmol). The reaction mixture is allowed to proceed at room temperature for about 6 hr. The reaction mixture is then filtered and concentrated and the residue resuspended in ethyl acetate and extracted with HCl (3M). The aqueous phase is basified with NaOH (10M) and then back-extracted with more ethyl acetate. The final ethyl acetate phase is washed with brine, dried over anhydrous MgSO$_4$ and concentrated. Thus the desired 2-(4-(4-chlorobenzyl)-piperazino-1-(2,3-dihydro-1H-1-indolyl)-1-ethanone (alternatively named 2-(4-(4-chlorobenzyl)

piperazinyl)-1-indolinylethan-1-one) is obtained as a light pink solid (1.3 g, 3.5 mmol) in 50% yield. Mp: 139.5–140° C. ¹H NMR (400 MHz, CDCl₃) d 8.23 ppm (d., 1 H, 8.8 Hz), 7.26 ppm (m., 4 H), 7.24 ppm (m., 2 H), 7.01 ppm (t., 1 H, 7.2 Hz), 4.16 ppm (t., 2 H, 8.4 Hz), 3.48 ppm (s, 2 H), 3.25 ppm (s., 2 H), 3.19 ppm (br. t., 2 H, 8.4 Hz), 2.64 ppm (br s, 4 H), 2.51 ppm (br. s., 4 H) and MS (CI) M⁺369.

The HBr salt of the title compound (Compound 19) is prepared from a methanolic solution (using 48% aqueous HBr), and recrystallized from ethanol/acetone to yield a white solid, mp: 258–260° C.

EXAMPLE 3

The following compounds are prepared essentially according to the procedures set forth above in Examples 1 and 2:

(a) 2-(4-(4-chlorobenzyl)piperazino-1-(2-methyl-2,3-dihydro-1H-1-indolyl)-1-ethanone (compound 3) (dihydrobromide salt: Compound 3a).

(b) 2-(4-(4-chlorobenzyl)piperazino-1-(1,2,3,4-tetrahydro-1-quinolinyl)-1-ethanone (Compound 4) (dihydrobromide salt: Compound 4a).

(c) 2-(4-(4-chlorobenzyl)piperazino-1-(3,4-dihydro-2H-benzo[b]1,4-oxazin-4-yl)-1-ethanone (Compound 5) (dihydrobromide salt: Compound 5a).

(d) 2-(4-(4-chlorobenzyl)-piperazino-1-(3,4-dihydro-2H-benzo[b]1,4-thiazin-4-yl)-1-ethanone (Compound 6) (hydrobromide salt: Compound 6a).

(e) 1-(2,2-dimethylindolinyl)-2-(4-(4-chlorobenzyl)-piperazinyl)ethan-1-one (Compound 7).

(f) 1-(2,2-dimethylindolinyl)-2-(4-(4-methylbenzyl)-piperazinyl)ethan-1-one (Compound 8).

(g) 1-(2-methylindolinyl)-2-(4-(4-methylbenzyl)-piperazinyl)ethan-1-one (Compound 9).

(h) 2-(4-[4-chlorobenzyl]piperazinyl)-1-spiro[cyclopentane-2,2'-indolin-1yl]ethanone (Compound 10).

(i) 2-(4-(4-chlorobenzyl)piperazinyl)-1-(4-fluoroindolinyl)ethan-1-one (Compound 11).

(j) 1-(5-chloro-2,2-dimethylindolinyl)-2-(4-(4-chlorobenzyl)piperazinyl)ethan-1-one (Compound 12).

(k) 2-(4-(5-chloro-2-methoxybenzyl)piperazinyl)-1-(2-methylindolinyl)ethan-1-one (Compound 13).

(l) 2-(4-(4-chlorobenzyl)piperazinyl)-1-(2-methylindolinyl)ethan-1–one (both resolved enantiomers)

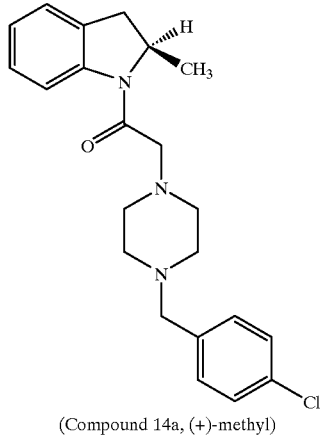

(Compound 14a, (+)-methyl)

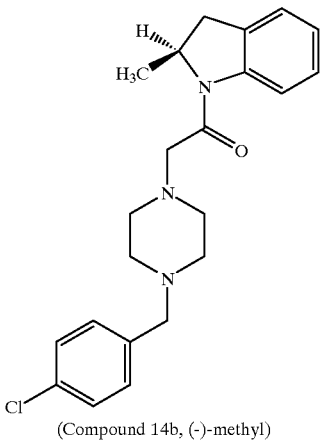

(Compound 14b, (-)-methyl)

(m) 1-indolinyl-2-(4-(4-methylbenzyl)piperazinyl) propan-1-one (Compound 15).

(n) 1-(2,2-dimethylindolinyl)-2-(4-(4-fluorobenzyl) piperazinyl)ethan-1-one (Compound 16).

(o) 2-(4-(4-chlorobenzyl)piperazinyl)-1-(7-methylindolinyl)ethan-1-one (Compound 17).

(p) 1-(6-chloroindolinyl)-2-(4-(4-chlorobenzyl) piperazinyl)ethan-1-one (Compound 18).

(q) N-butyl-2-(4-(4-chlorobenzyl)piperazinyl)-N-phenylethanamide (Compound 2) (dihydrobromide salt: Compound 2a).

EXAMPLE 4

Compound 1

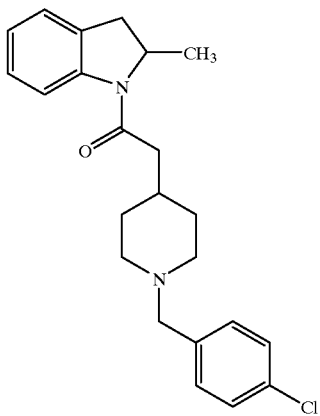

Ethyl-4-pyridylacetate (5 g) is dissolved in ethanol (30 mL), treated with platinum oxide catalyst (30 mg) and hydrogenated on a Parr apparatus for 4 hr. The catalyst is filtered off and the ethyl-4-piperidinylacetate is isolated by removal of the solvent under vacuum. This material is then dissolved in acetonitrile (50 mL) and treated with 4-chlorobenzyl chloride (4.9 g) and sodium carbonate (10 g). The resulting mixture is heated in methanol (30 mL) and treated with a solution of lithium hydroxide (2 g) in water (10 mL). The mixture is allowed to stand overnight. Addition of 47.6 mL of 1 N HCl solution followed by concentration and extraction of the residue with chloroform provides the desired 1-(4-chlorobenzyl)-4-piperidylacetic acid. A portion of this material (1 g) is dissolved in methylene chloride and treated with 1,1'-carbonyldiimidazole (0.65 g) and allowed to stand overnight. This solution is then treated with 2-methylindoline (0.5 g). After 2 h the resulting mixture is washed 3 times with water dried and concentrated. Purification by column chromatography on silica gel provides 1.2 g of the desired 2-(1-[4-chlorobenzyl]piperidin-4-yl)-1-(2-methylindolin-1-yl)-1-ethanone (Compound 1). The dihydrochloride salt is subsequently prepared (Compound 1a).

EXAMPLE 5
Assay for $D_2$ and $D_4$ Receptor Binding Activity

The pharmaceutical utility of compounds of this invention is indicated by the assays for dopamine receptor subtype affinity described below.

Pellets of CHO cells containing human $D_2$ or $D_4$ receptors cloned from c-DNA are used for assays (Tallman, J. F. et. al., J. Pharm. Exp. Ther., 1997, 282, 1011). The cloned membranes are homogenized in 100 volumes (wt/vol) of 0.05M Tris-HCl buffer at 4° C. and pH 7.4 containing 120 mM NaCl, 1 mM EDTA and 5 mM $MgCl_2$. The samples were centrifuged at 48,000×g then re-suspended and re-homogenized. The final tissue sample is kept frozen until use. The tissue is resuspended 1:20 (wt/vol) in 0.05M Tris-HCl buffer containing 120 mM NaCl prior to use.

Incubations were carried out at 48° C. and contain 0.4 ml of tissue sample, 0.5 nM $^3$H-YM 09151-2 (Nemonapride, cis-5-Chloro-2-methoxy-4-(methylamino)-N-(2-methyl-2-(phenylmethyl)-3-pyrrolidinyl)benzamide) and the compound of interest in a total incubation of 1.0 ml. Non-specific binding is defined as that binding found in the presence of 1 mM spiperone; without further additions, nonspecific binding is less than 20% of total binding. Binding characteristics for examples of compounds encompassed within Formula I for the $D_2$ and $D_4$ receptor subtypes are shown in Table 2 for rat striatal homogenates.

TABLE 2

| Compound No.[1] | $D_4$ $K_I$ (nM) | $D_2$ $K_I$ (nM) |
|---|---|---|
| 1 | 7 | 92 |
| 2 | 154 | ND |
| 3 | 0.7 | 74 |
| 4 | 47 | 10,000 |
| 5 | 429 | 2610 |
| 6 | 14.2 | 10,000 |

[1]Compound numbers relate to the compounds shown in Table 1.

The binding constants of compounds of Formula I for the $D_4$ receptor, expressed in nM, generally range from about 0.1 nanomolar (nM) to about 500 nanomolar (nM). Preferred compounds have binding constraints of from about 0.1 to 100 nM. Preferred compounds typically have binding constants for the $D_2$ receptor at least about 10–15 times that of the $D_4$ binding constant. Thus, the compounds of the invention are generally at least about 10 time more selective for the $D_4$ receptor than the $D_2$ receptor. Preferably, these compounds are at least 20, and more preferably at least 25–50, times more selective for the $D_4$ receptor than the $D_2$ receptor. Most preferably, the compounds of Formula I are at least 100 times more selective for the $D_4$ receptor than the $D_2$ receptor.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of the formula:

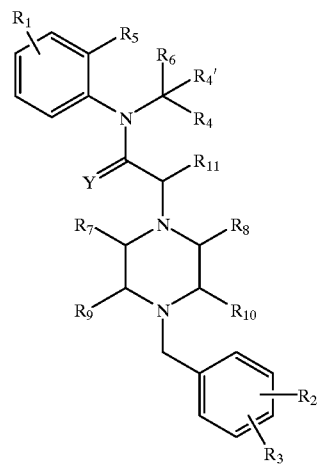

or pharmaceutically acceptable addition salts thereof wherein:

Y represents oxygen or sulfur;

$R_1$, $R_2$ and $R_3$ independently represent hydrogen, halogen, hydroxy, $C_1$–$C_6$ alkoxy, $C_1$–$C_6$ alkyl, trifluoromethyl or trifluoromethoxy;

$R_4$ and $R_4'$ independently represent hydrogen or $C_1$–$C_6$ alkyl; or $R_4$ and $R_4'$ together with the atom to which they are attached form a ring having from 3–7 members;

$R_5$ represents hydrogen, $C_1$–$C_6$ alkyl, $C_1$–$C_6$ alkoxy, or $C_1$–$C_6$ alkylthio;

$R_6$ is hydrogen or $C_1$–$C_6$ alkyl; or $R_5$ and $R_6$ together represent $C_1$–$C_5$ alkylene, $C_1$–$C_5$ alkyleneoxy, $C_1$–$C_5$ alkylenethio where the oxygen or sulfur atoms are immediately adjacent the phenyl ring, and together with the atoms to which they are attached form a ring having from 5–9 members; and $R_7$, $R_8$, $R_9$, $R_{10}$, and $R_{11}$ independently represent hydrogen or $C_1$–$C_6$ alkyl, provided that not both $R_4$ and $R_4'$ are hydrogen when $R_5$ and $R_6$ do not together represent $C_1$–$C_5$ alkylene, $C_1$–$C_5$ alkyleneoxy, or $C_1$–$C_5$ alkylenethio.

2. A compound according to claim 1, wherein only one of $R_2$ and $R_3$ is hydrogen.

3. A compound according to claim 1, having the formula:

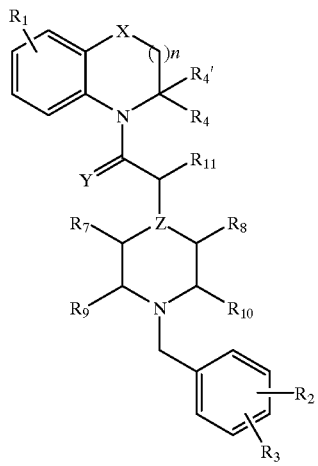

wherein X represents oxygen, sulfur, or CH;

Y is oxygen or sulfur;

Z is nitrogen;

n is zero or an integer of from 1–4;

$R_1$, $R_2$ and $R_3$ independently represent hydrogen, halogen, hydroxy, $C_1$–$C_6$ alkoxy, $C_1$–$C_6$ alkyl, trifluoromethyl or trifluoromethoxy;

$R_4$ and $R_4'$ independently represent hydrogen or $C_1$–$C_6$ alkyl; or $R_4$ and $R_4'$ together with the atom to which they are attached form a ring having from 3–7 members;

$R_7$, $R_8$, $R_9$, $R_{10}$ and $R_{11}$ independently represent hydrogen or $C_1$–$C_6$ alkyl.

4. A compound according to claim 1, having the formula:

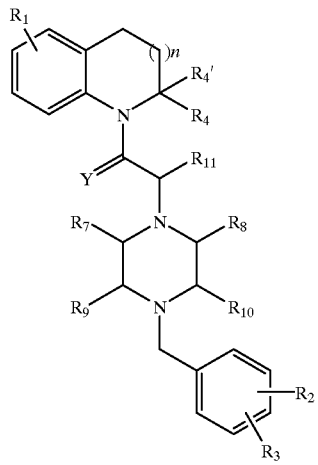

wherein n is an integer of from 1–4; Y is oxygen; and $R_1$, $R_2$, $R_3$, $R_4$, $R_4'$ $R_7$, $R_8$, $R_9$, $R_{10}$, and $R_{11}$ are as defined above in claim 1.

5. A compound according to claim 1, having the formula:

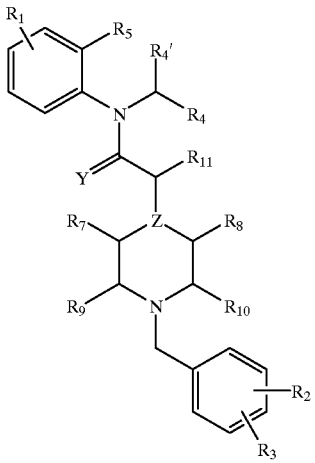

wherein

Z is nitrogen;

$R_4$ and $R_4'$ together with the atom to which they are attached form a ring having from 3–7 members;

$R_5$ represents hydrogen, $C_1$–$C_6$ alkyl, $C_1$–$C_6$ alkoxy, or $C_1$–$C_6$ alkylthio; and Y, $R_1$, $R_2$, $R_3$, $R_7$, $R_8$, $R_9$, $R_{10}$, and $R_{11}$ are as defined above in claim 1.

6. A compound according to claim 1, having the formula:

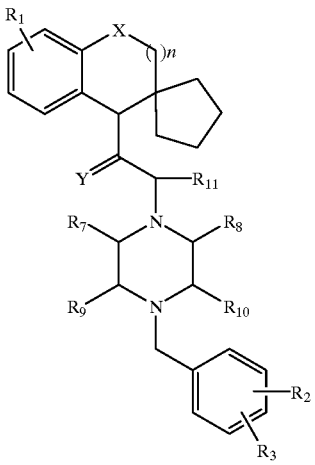

wherein n is an integer of from 1–4; and Y, X, $R_1$, $R_2$, $R_3$, $R_7$, $R_8$, $R_9$, $R_{10}$, and $R_{11}$ are as defined above in claim 1.

7. A compound according to claim 6, wherein Y is oxygen, $R_1$ is hydrogen or halogen, and $R_2$ and $R_3$ are independently selected from hydrogen, $C_1$–$C_6$ alkyl, and halogen.

8. A compound according to claim 7, wherein not both of $R_2$ and $R_3$ are hydrogen simultaneously.

9. A compound according to claim 7, wherein $R_2$ is hydrogen and $R_3$ is methyl, chloro or fluoro.

10. A compound according to claim 9, wherein $R_3$ is a methyl, chloro or fluoro group in the 4 position on the phenyl ring.

11. A compound according to claim 10, wherein n is 0.

12. A compound according to claim 5, wherein Y is oxygen, $R_1$ is hydrogen or halogen, and $R_2$ and $R_3$ are independently selected from hydrogen, $C_1$–$C_6$ alkyl, and halogen.

13. A compound according to claim 1, which is 2-(4-(4-chlorobenzyl)piperazinyl)-1-indolinylethan-1-one.

14. A compound according to claim 1, which is 2-(4-(4-chlorobenzyl)piperazino-1-(2-methyl-2,3-dihydro-1H-1-indolyl)-1-ethanone.

15. A compound according to claim 1, which is 2-(4-(4-chlorobenzyl)piperazino-1-(1,2,3,4-tetrahydro-1-quinolinyl)-1-ethanone.

16. A compound according to claim 1, which is 2-(4-(4-chlorobenzyl)piperazino-1-(3,4-dihydro-2H-benzo[b]1,4-oxazin-4-yl)-1-ethanone.

17. A compound according to claim 1, which is 2-(4-(4-chlorobenzyl)-piperazino-1-(3,4-dihydro-2H-benzo[b]1,4-thiazin-4-yl)-1-ethanone.

18. A compound according to claim 1, which is 1-(2,2-dimethylindolinyl)-2-(4-(4-chlorobenzyl)piperazinyl)ethan-1-one.

19. A compound according to claim 1, which is 1-(2,2-dimethylindolinyl)-2-(4-(4-methylbenzyl)-piperazinyl)ethan-1-one.

20. A compound according to claim 1, which is 1-(2-methylindolininy-2-(4-(4-methylbenzyl)-piperazinyl)ethan-1-one.

21. A compound according to claim 1, which is 2-(4-(4-chlorobenzyl)piperazinyl)-1-spiro [cyclopentane-2,2'-indolin-1-yl]ethanone.

22. A compound according to claim 1, which is 2-(4-(4-chlorobenzyl)piperazinyl)-1-(4-fluoroindolinyl)ethan-1-one.

23. A compound according to claim 1, which is 1-(5-chloro-2,2-dimethylindolinyl)-2-(4-(4-chlorobenzyl) piperazinyl) ethan-1-one.

24. A compound according to claim 1, which is 2-(4-(5-chloro-2-methoxybenzyl)piperazinyl)-1-(2-methylindolinyl) ethan-1-one.

25. A compound according to claim 1, which is

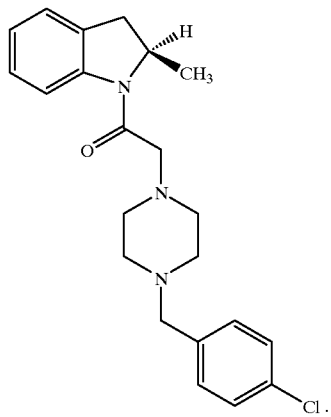

26. A compound according to claim 1, which is

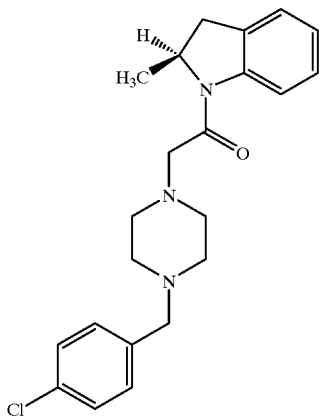

27. A compound according to claim 1, which is 1-indolinyl-2-(4-(4-methylbenzyl)piperazinyl)propan-1-one.

28. A compound according to claim 1, which is 1-(2,2-dimethylindolinyl)-2-(4-(4-fluorobenzyl)piperazinyl)ethan-1-one.

29. A compound according to claim 1, which is 2-(4-(4-chlorobenzyl)piperazinyl)-1-(7-methylindolinyl)ethan-1-one.

30. A compound according to claim 1, which is 1-(6-chloroindolinyl)-2-(4-(4-chlorobenzyl)piperazinyl)ethan-1-one.

31. A compound according to claim 1, which is 1-(4-(4-chlorobenzyl)-piperazinyl)-2-indolinylethan-1-one.

32. A compound according to claim 1, which is N-butyl-2-(4-(4-chlorobenzyl)piperazinyl)-N-phenylethanamide.

* * * * *